United States Patent
Domingos

(10) Patent No.: US 10,548,635 B2
(45) Date of Patent: Feb. 4, 2020

(54) FILE WITH REMOVABLE PLASTIC ABRASIVE SLEEVE

(71) Applicant: CONVEXA LLC, Surfside, FL (US)

(72) Inventor: Fabio Maluf Domingos, Surfside, FL (US)

(73) Assignee: CONVEXA LLC, Surfside, FL (US)

(*) Notice: Subject to any disclaimer, the term of this patent is extended or adjusted under 35 U.S.C. 154(b) by 204 days.

(21) Appl. No.: 15/826,448

(22) Filed: Nov. 29, 2017

(65) Prior Publication Data

US 2018/0177528 A1   Jun. 28, 2018

Related U.S. Application Data

(60) Provisional application No. 62/437,701, filed on Dec. 22, 2016.

(51) Int. Cl.
*A61B 17/54* (2006.01)
*A61B 17/32* (2006.01)

(52) U.S. Cl.
CPC .............. *A61B 17/54* (2013.01); *A61B 17/32* (2013.01); *A61B 2017/320004* (2013.01); *A61B 2017/320008* (2013.01)

(58) Field of Classification Search
CPC .................................. A61B 17/54; A61B 17/32
See application file for complete search history.

(56) References Cited

U.S. PATENT DOCUMENTS

| | | | |
|---|---|---|---|
| 5,116,346 A * | 5/1992 | Yeh | A61B 17/32093 16/430 |
| 5,335,373 A * | 8/1994 | Dresdner, Jr. | A61B 42/10 2/161.7 |
| 2007/0250079 A1 | 10/2007 | Kern | |
| 2010/0037906 A1* | 2/2010 | Ionis | A61B 17/54 132/76.5 |
| 2010/0145359 A1* | 6/2010 | Keller | A61B 17/54 606/131 |
| 2013/0056015 A1* | 3/2013 | Wang | A61B 17/54 132/76.4 |

* cited by examiner

*Primary Examiner* — Richard G Louis
(74) *Attorney, Agent, or Firm* — Joseph Suhadolnik

(57) ABSTRACT

A lightweight, handheld tool for performing cosmetic dermabrasion comprises a tool body, which is inserted into a disposable sleeve during use, which sleeve has an abrasive with an exposed grit adhered to at least a portion of the exterior, which abrasive contacts the surface being undergoing dermabrasion. The sleeve envelops the tool body, protecting the tool body from the transference of bacteria and particulates during dermabrasion, reducing the need for regular sterilization of the reusable tool body. After use, the disposable sleeve is readily discarded and can be replaced by a new sleeve for the next use.

16 Claims, 3 Drawing Sheets

FILE WITH REMOVABLE PLASTIC ABRASIVE SLEEVE

FIELD OF THE INVENTION

The present invention provides a tool useful for cleaning and removing dead and calloused skin, e.g., on feet, which tool comprises a reusable tool body and a disposable sleeve comprising an adhered abrasive surface or pad, which sleeve envelops the tool body during use to act as a barrier lessening the transference of bacteria and particulates to the tool body within and reducing the need for regular sterilization of the reusable tool body.

BACKGROUND

Human skin is an organ that protects our body from the environment around us. Human skin consists of 3 layers, the epidermis, dermis, and deeper subcutaneous tissue. The epidermis is the outermost layer of skin that provides a barrier to our environment as well as creates our skin tone. Cleaning away particulates on the epidermis allows for the skin to appear and feel healthier as well as youthful-looking. If the skin is clean, then the pores remain unclogged, allowing it to function properly.

Without proper removal of skin overgrowth on the feet, such skin can cause significant pain resulting from cracks that form in the dry skin overgrowth and opens the skin to possible infection. The surface of the skin is constantly battling bacteria so any opening could quickly become infected. To remove skin overgrowths a typical user would use a traditional abrasive surface attached directly to a handle, which becomes either costly to throw away, or time consuming and difficult to sterilize.

Over the past few years, distressed nail salon customers have filed lawsuits against nail salon owners for improper or inadequate sanitizing practices. Some customers have been left with infections as a result of unclean conditions, some as serious as Hepatitis, which, in some circumstances, have turned deadly. Reports of similar incidents resulting from unsanitary nail salons have occurred throughout the United States. Salon customers may inadvertently be exposed to infections resulting from improper sterilization of nail equipment. Foot baths used in nail salons contain a variety of bacteria that can cause a client to develop infections and nail fungus can spread in a salon if foot baths and instruments aren't cleaned properly.

Dermabrasion clears away dead skin, dander, and flakes to allow skin to function properly. Dermabrasion does not use water, as in traditional salon style manicures and pedicures, and is able to drastically lower the concentration of bacteria when performing these spa services. As discussed above however, any method for removing the dead skin with an abrasive tool requires that the tool be properly sterilized. In order to reduce costs or inconvenience associated with re-sterilizing reusable tools, or the expense of disposing a tool after limited use, efforts have been made to develop less expensive, disposable, abrasive tools for the removal of dead skin.

US Pat. Appl. Pub. 2010/0037906 discloses a pedicure file comprising an ovate housing having a hollow interior formed by two identically configured cap members, wherein the outer surfaces of the housing are designed to support removable and disposable abrasive pads thereon. The pads are employed to scrape away calluses from the skin.

US Pat. Appl. Pub. 2007/0250079 discloses a lightweight hand-held tool for performing cosmetic dermabrasion comprising a handle of aluminum tubing, a flattened head of aluminum and at least one removable pad attached to the flattened head, wherein the flattened head is covered by hook and loop fasteners for attachment to the removable pad that also contains hook and loop fasteners.

US Pat. Appl. Pub. 2010/0145359 discloses a callus rasp comprising a rasp body having a handle portion, a blade portion and an abrasive surface with a particulate grit exposed therefrom, and an adhesive to secure the abrasive surface to the blade portion of the rasp body. The abrasive surface is pre-adhered with the adhesive and a peelable backing layer over the adhesive together form a foil. The foil and rasp body are sterilized before joinder. After use, the abrasive surface is removed so that the rasp body can be reused with a new abrasive surface after sterilization.

Despite these efforts, a less expensive, readily sterilized, tool for skin removal is still needed.

SUMMARY OF THE INVENTION

The present invention provides a hand-held tool for performing cosmetic dermabrasion comprising:

a) a reusable tool body comprising a handle and flattened head, wherein the flattened head typically comprises one or more depressions, and (b) a removable disposable sleeve, sized to envelope the entire reusable tool body, having an abrasive material adhered to at least a portion of an outward facing side of the sleeve, into which sleeve the body is inserted for use.

The disposable sleeve has an upper end, which is sealed, and an open lower end through which the tool body is inserted, after which the lower end is closed. One significant advantage of the invention is that the sleeve separates the tool body from the skin being treated, reducing or eliminating transference of bacteria to the tool body during use. After use, the sleeve can be removed and disposed, while the body can be reused with no significant sterilization equipment needed.

The body of the inventive tool can be conveniently made from a polymeric material, such as a thermoplastic, elastomeric or thermoset polymer, e.g., polystyrene, by any known molding or shaping process. The body's has a lower portion comprising a handle designed for easy gripping, and an upper portion comprising a flattened head. The flattened head has two flattened sides and a depression in one or both of the flattened sides.

The sleeve comprises a wrapper composed of a thin film or foil, typically a polymeric film or foil, having an open lower end and an upper portion having a closed upper end, with an abrasive material, e.g., an abrasive pad, adhered to the exterior, i.e., outer side, on the upper portion of the wrapper. The adhered abrasive material contacts the surface that is subjected to dermabrasion.

The sleeve fits over the tool body, typically sliding over both the handle and the flattened head, with the lower portion of the sleeve covering the handle and the upper end of the sleeve covering the flattened head. The portion of the sleeve to which the abrasive material is adhered aligns with a depression in the flattened head. There is no particular limitation on the size or shape of the abrasive pad, or the area covered by the adhered abrasive, and more than one area of the sleeve may have abrasive material adhered thereon. Generally, the shape and proportions of the abrasive pad will be the same or similar to the size and shape of a depression in the flattened head, e.g., the abrasive pad fits into the depression.

The tool of the invention can be used to remove any skin overgrowth where an abrasive surface would be needed, including skin near finger or toe nails, and is particularly useful for dermabrasion of the feet.

Various embodiments of the invention include the tool described above comprising the tool body inside the disposable sleeve, a kit comprising the tool body of the invention and the sleeve of the invention as separate items, and a method for performing dermabrasion comprising the steps of inserting the tool body of the invention into the sleeve of the invention so that the abrasive material of the sleeve is aligned with a depression in the flattened head of the tool body, and applying the adhered abrasive material to skin to remove dry skin and particulates.

Attaching an abrasive material to the exterior of a relatively low cost disposable plastic sleeve that covers the reusable tool body during use according to the present invention provides a tool that is more easily sanitized while making dermabrasion significantly less expensive.

DESCRIPTION OF THE INVENTION

The dermabrasion tool of the invention comprises a reusable body and a disposable sleeve. The sleeve fits over the body, protecting the body from outside contact during use, by separating the reusable tool body from the bacteria associated with the cleaning and removing of dead skin, e.g., skin on feet, and comprises an abrasive that contacts the skin being abraded. Use of the present invention reduces or eliminates the need for rigorous sterilization of the tool body between uses.

The lower portion of the body comprises a handle designed for easy gripping, and the upper portion of the body comprises a flattened head with a depression, which depression aligns with, and supports the abrasive of the sleeve in use when in use. The depression is slightly curved to achieve the contours of the foot, reaching arch and heel portions to better exfoliate the skin in those areas. The sleeve is oriented so that the abrasive pad is in association with the curved portion to better reach the area desired. The tool body may comprise more than one depression and more than one portion of the sleeve may have an abrasive or abrasive pad adhered thereto.

Figure 1:
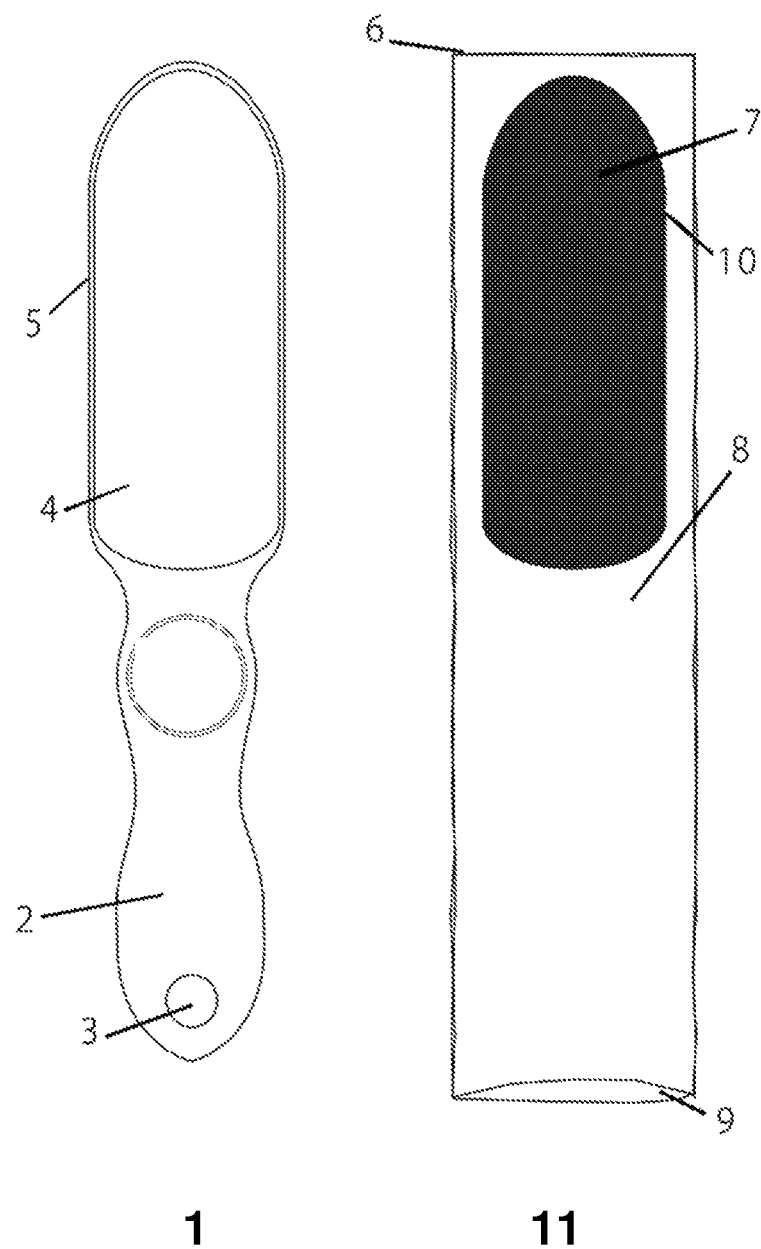
FIG. 1 shows a tool body 1, and disposable sleeve of the invention.

FIG. 1 shows one embodiment of the tool body (1) and sleeve (11). The upper portion of the tool body comprises a flattened head (5) with a slight depression (4) to accommodate the abrasive pad (7) of the sleeve (11). In the embodiment shown, the flattened head (5) has an oblong arched shape and the depression (4) has an oval shape. The lower portion (2) of the tool body comprises a handle with grip, typically a molded ergonomic grip, shown here with a round end. The embodiment shown in FIG. 1 includes an optional hole (3) for securing the tool body when not in use. The body can also comprise other features including, color and other design features, intended to make the tool more attractive or easier to use.

The tool body has a length, width and thickness that makes the tool comfortable in the hand, strong enough for multiple uses, and of a size convenient for use on feet, hands, etc. For example, in one embodiment, the body is from 7 to 12 inches long and from 1 to 3 inches wide, at the widest point. The lower 30 to 70% or 40 to 60%, e.g. 45 to 55%, of the body comprises the handle and the upper 30 to 70% or 40 to 60%, e.g. 45 to 55%, comprises the flattened head. In the one embodiment shown, the grip is not as wide as the flattened head and is shaped to comprise various widths. In certain embodiments the body is from 9 to 10 inches long and from 1.5 to 2.5 inches wide, at the widest point.

The body is conveniently prepared from a polymeric material using known molding methods, e.g., cast molding, compression molding, injection molding, etc., although other materials or methods of production may be used. Typically, the body is a molded article comprising one or more polymeric materials, such as polystyrene, modified polystyrenes and polystyrene blends, e.g., oriented polystyrene, impact modified polystyrene or ABS, polyolefin, rubber, polyamide, acrylic, epoxy resin, polyester, polyurethane, polycarbonate, polyacetal, polyvinyl chloride, and the like. The polymeric material can be a homo-polymer, e.g., polyethylene or polypropylene, or a co-polymer, e.g., an ethylene/propylene copolymer.

Even though the body is protected from outside contact, e.g., from contact with the surface being abraded or other environmental contaminates, during use, it is still preferable that the body be made from a readily sterilized material, for example, in certain embodiments the body is prepared from polystyrene.

In one particular embodiment, the body is a polystyrene body of FIG. 1, made as a single piece. As an example to illustrate one particular set of proportions, the body can be 9.75 inches long, 2 inches wide, having a handle portion that is 5 inches long comprising a molded grip with several widths, the smallest width being 1.3 inches.

FIG. 1 also shows a disposable plastic sleeve (11) of the invention, with closed upper end (6), open lower end (9) an abrasive material (7) adhered to the exterior of the upper portion of the sleeve with adhesive (10). The sleeve has an interior region or void into which the tool body is inserted.

Figure 2:
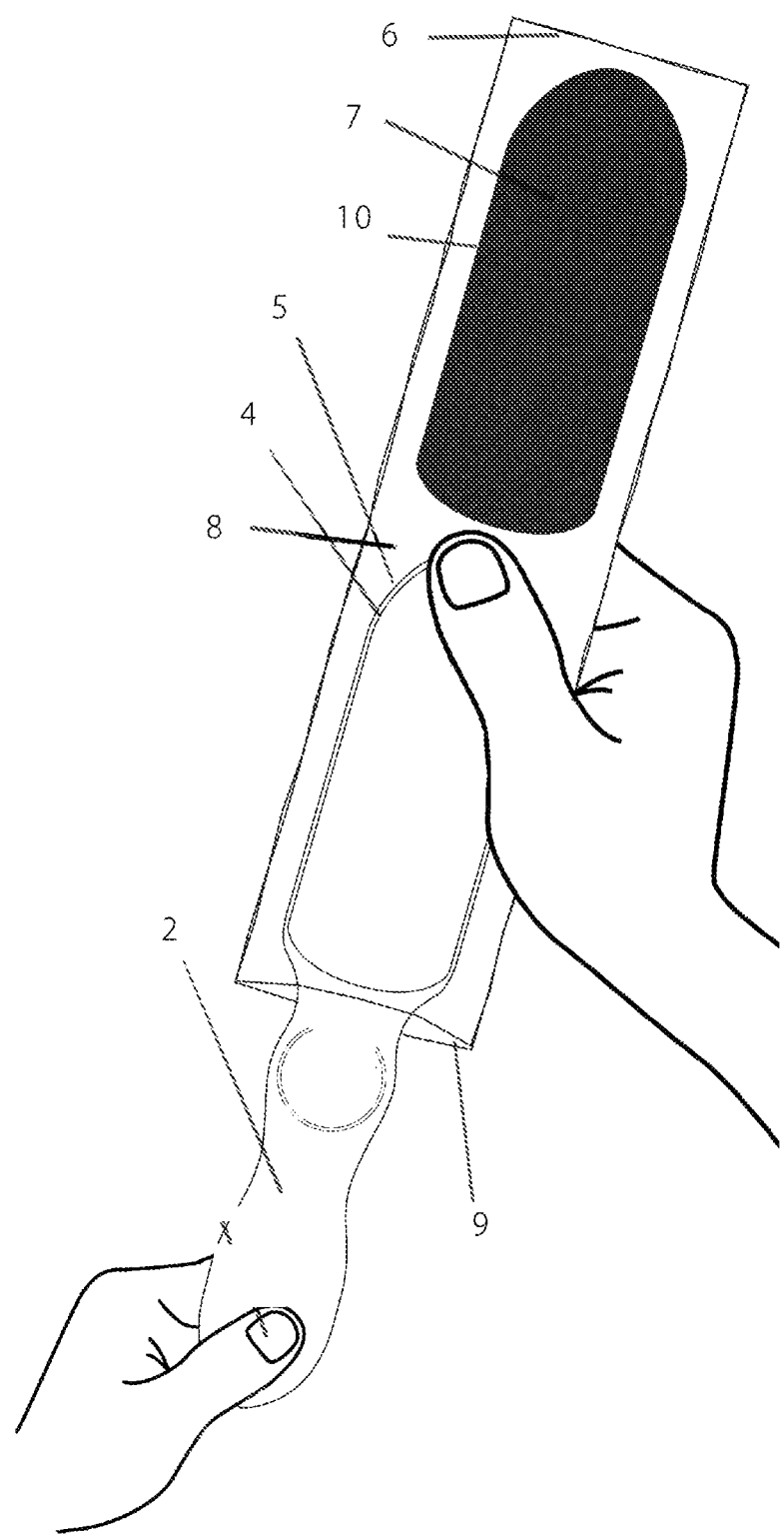
FIG. 2 shows the sleeve being applied over the tool body.
Figure 3:
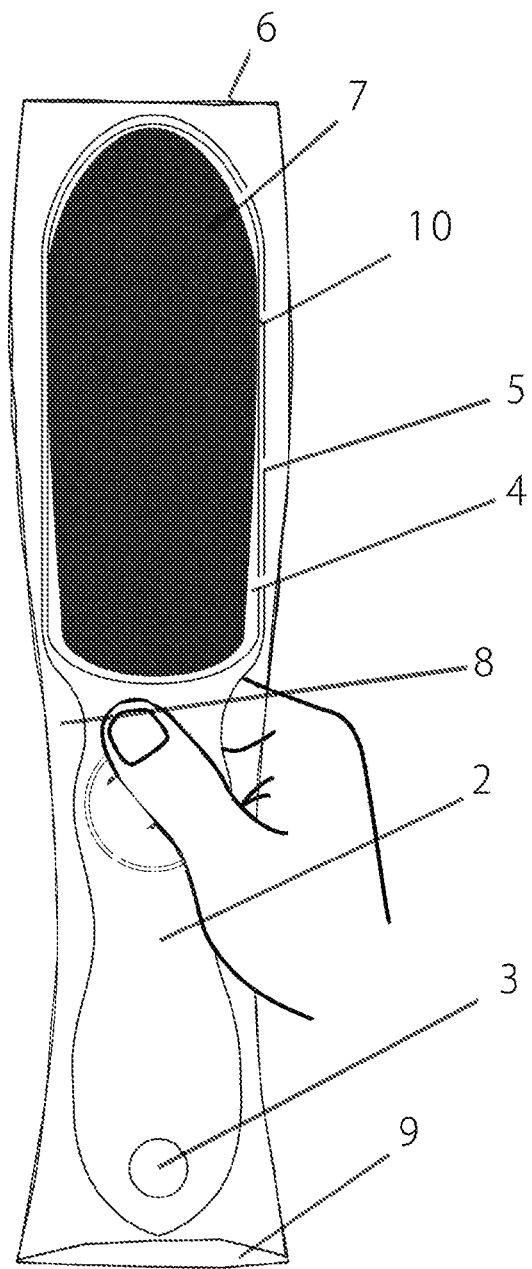
FIG. 3 shows the body within the sleeve, with the abrasive over a depression on the flattened head.

The sleeve comprises a wrapper (8), typically formed from a plastic film or foil, to which the abrasive material is adhered. The sleeve of FIG. 1 has an elongated shape. The wall of the wrapper is thin, e.g., from about 0.02 to 0.15 mm thick, typically from about 0.03 to about 0.1 mm thick, and has enough flexibility so that it can slide over the body and adapt at least to some extent to the shape of the body. The overall length and width of the sleeve are slightly greater than that dimensions of the body. FIG. 2 is an illustration of a plastic sleeve being placed over a tool body of the invention, showing the slightly greater outer dimensions of the sleeve. For example, in one embodiment where the tool body is from 7 to 12 inches long and from 1 to 3 inches wide at the widest point, the sleeve is from 7.2 to 12.5 inches long and from 1.2 to 3.3 inches wide.

Like the tool body, the sleeve wrapper is conveniently prepared from a polymeric material using known methods, including a variety of molding methods, e.g., cast molding, compression molding, injection molding, etc. However, due to the thin wall of the sleeve, a variety of film forming methods can also be employed. For example, the wrapper can be made by first preparing a film by casting, extrusion, compression molding, drawn down, or any other known film forming process, which film is further processed to form the wrapper into the shape of the sleeve and to adhere the abrasive material.

The wrapper is prepared from one or more polymeric materials such as polystyrene, modified polystyrenes and polystyrene blends, e.g., oriented polystyrene, impact modified polystyrene or ABS, polyolefin, rubber, polyamide, acrylic, epoxy resin, polyester, polyurethane, polycarbonate, polyacetal, polyvinyl chloride, and the like. The polymeric material can be a homo-polymer, e.g., polyethylene or polypropylene, or a co-polymer, e.g., an ethylene/propylene copolymer.

Portions of the sleeve contact the surface being abraded and must be capable of being readily sterilized. Therefore, the polymer chosen for the wrapper must be capable of forming a thin section that is strong enough to endure the process of dermabrasion while supporting the abrasive material, and must also be amenable to sterilization techniques. In most embodiments the sleeve is clear. For example, in certain embodiments the body is prepared from polystyrene, modified polystyrene, polystyrene blend, polyethylene or polypropylene, and typically, the sleeve wrapper is prepared from oriented polystyrene.

The overall shape of the sleeve, with the interior void and single opening, can be prepared by directly molding the polymer of the wrapper into the final shape in a single step, e.g., by compression, injection or cast molding; or a multi-step process can be employed. For example, an open tube can be prepared, either by directly in a molding process or by sealing two opposing sides of a film, and sealing one of the open ends. The sleeve can also be prepared from two or more separately prepared films that are joined to form the sleeve of FIG. 2.

In one particular embodiment, the sleeve is a sleeve of FIG. 1, comprising a clear, oriented polystyrene wrapper. As an example to illustrate one particular set of proportions, the sleeve can be 10 inches long, 2.2 inches wide, and 0.05 mm thick, to which has been adhered an abrasive pad having an elongated oval shape that is about 4.8 inches long and 1.6 inches wide. In many embodiments, the adhesive pad has a shape that is very similar or identical to that of the depression in the flattened head of the tool body.

Abrasive materials useful in the practice of dermabrasion are well known and any such material can be employed. The abrasive is adhered to the wrapper by means of an acceptable adhesive, e.g., glue, which adhesive must withstand sterilization while maintaining adequate adhesion to both the abrasive and the polymer of the wrapper. Such glues are also known and can be readily selected by one of ordinary skill in the art.

The step of adhering the abrasive material to the wrapper can take place at any stage of the process after the initial processing of the wrapper polymer, i.e., after molding the polymer to form the sleeve with interior void, tube or film as described above. In use, the body of the tool is inserted into the sleeve at lower end (9) as shown in FIG. 2. The lower portion of the sleeve, e.g., the portion over the lower, handle portion of the body, can be twisted with the user's hand to order to firmly maintain the sleeve's desired position, not allowing it to move freely during the process. The sleeve is sterilized before skin contact, and this can be done before or after insertion of the tool body using any acceptable method.

The handheld tool of the invention is readily incorporated into methods for cleaning and performing cosmetic dermabrasion. While the invention has been described by specific examples and embodiments, there is no intent to limit the inventive concept except as set forth in the following claims.

What is claimed:

1. A handheld tool for performing cosmetic dermabrasion comprising: (a) a reusable tool body comprising a handle and a flattened head, wherein the flattened contains one or more depressions, and (b) a removable disposable sleeve, sealed at one end and open at an end opposite the sealed end, having an abrasive material adhered to at least a portion of an outward facing side of the sleeve, which sleeve envelopes the tool body during use wherein the abrasive material adhered to the sleeve is aligned with one of the one or more depressions in the flattened head of the tool body.

2. The tool according to claim 1 wherein the flattened head has an oblong arched shape.

3. The tool according to claim 1 wherein the one or more depressions in the flattened head has an oval shape.

4. The tool according to claim 1 wherein the abrasive material adhered to the sleeve has a shape that is similar to, or the same as, one of the one or more depressions of the flattened head to which the adhesive is aligned.

5. The tool according to claim 1 wherein the tool body comprises one or more polymeric material.

6. The tool according to claim 1 wherein the removable sleeve comprises a wrapper composed of polymeric film to which the abrasive material is adhered.

7. The tool according to claim 6 wherein the tool body and wrapper comprise one or more polymer selected from the group consisting of polystyrenes, impact modified polystyrenes, polystyrene blends, polyolefins, rubbers, polyamides, polyacrylates, epoxy resins, polyesters, polyurethanes, polycarbonates, polyacetals and polyvinyl chloride.

8. The tool according to claim 7 wherein the tool body is prepared from polystyrene.

9. The tool according to claim 7 wherein the wrapper comprises oriented polystyrene.

10. A kit comprising the reusable tool body and removable sleeve of claim 1 as separate items.

11. A kit comprising the reusable tool body and removable sleeve of claim 2 as separate items.

12. A kit comprising the reusable tool body and removable sleeve of claim 4 as separate items.

13. A kit comprising the reusable tool body and removable sleeve of claim 7 as separate items.

14. A kit comprising the reusable tool body and removable sleeve of claim 8 as separate items.

15. A kit comprising the reusable tool body and removable sleeve of claim 9 as separate items.

16. A method for performing cosmetic dermabrasion using a kit comprising a) a reusable tool body and b) a removable disposable sleeve as separate items, wherein the reusable tool body comprises a handle and a flattened head, wherein the flattened head contains one or more depressions, and wherein the tool body comprises one or more polymer selected from the group consisting of polystyrenes, impact modified polystyrenes, polystyrene blends, polyolefins, rubbers, polyamides, polyacrylates, epoxy resins, polyesters, polyurethanes, polycarbonates, polyacetals and polyvinyl chloride, and the removable disposable sleeve comprises a wrapper comprising oriented polystyrene, which disposable sleeve is sealed at one end and open at an end opposite the sealed end, having an abrasive material adhered to at least a portion of an outward facing side of the sleeve, which sleeve envelopes the tool body during use wherein the abrasive material adhered to the sleeve is aligned with one of the one or more depressions in the flattened head of the tool body, the method comprising inserting the tool body into the sleeve so that the abrasive material is aligned with a depression in the flattened head, and applying the adhered abrasive to skin to remove dry skin and particulates.

* * * * *